United States Patent [19]

Reising et al.

[11] Patent Number: 4,988,344
[45] Date of Patent: Jan. 29, 1991

[54] ABSORBENT ARTICLES WITH MULTIPLE LAYER ABSORBENT LAYERS

[75] Inventors: George S. Reising, Batavia; Bruce H. Bergman, Mason; Sandra H. Clear, Deerfield Township, Hamilton County; Susan E. Guinn, Colerain Township, Hamilton County; Rolando Gomez-Santiago, Cincinnati, all of Ohio

[73] Assignee: The Procter & Gamble Company, Cincinnati, Ohio

[21] Appl. No.: 198,032

[22] Filed: May 24, 1988

[51] Int. Cl.$^5$ .............................................. A61F 13/15
[52] U.S. Cl. .................................... 604/368; 604/378; 604/380; 604/358
[58] Field of Search ..................... 604/368, 378, 385.1, 604/385.2, 358, 380

[56] References Cited

U.S. PATENT DOCUMENTS

| | | |
|---|---|---|
| 810,120 | 1/1906 | Green . |
| 2,043,325 | 6/1936 | Jackson . |
| 3,029,817 | 4/1962 | Harwood et al. . |
| 3,046,986 | 7/1962 | Harwood . |
| 3,371,667 | 3/1968 | Morse . |
| 3,386,442 | 6/1968 | Sabee ................................. 604/378 |
| 3,441,023 | 4/1969 | Rijssenbeek . |
| 3,441,024 | 4/1969 | Ralph . |
| 3,491,759 | 1/1970 | Samuel . |
| 3,593,716 | 7/1971 | Vogt . |
| 3,593,717 | 7/1971 | Jones . |
| 3,620,894 | 11/1971 | Osten . |
| 3,665,920 | 5/1972 | Davis . |
| 3,731,688 | 5/1973 | Litt et al. . |
| 3,759,262 | 9/1973 | Jones . |
| 3,844,288 | 10/1974 | Kiela . |
| 3,889,679 | 6/1975 | Taylor . |
| 3,916,900 | 11/1975 | Breyer et al. ...................... 604/368 |
| 3,934,558 | 1/1976 | Mesek et al. . |
| 3,987,792 | 10/1976 | Hernandez et al. . |
| 4,027,672 | 6/1977 | Karami . |
| 4,173,046 | 11/1979 | Gallagher . |
| 4,285,342 | 8/1981 | Mesek . |
| 4,289,130 | 9/1981 | Usami et al. . |
| 4,381,782 | 5/1983 | Mazurak et al. . |
| 4,381,783 | 5/1983 | Elias ................................... 604/368 |
| 4,397,644 | 8/1983 | Matthews et al. . |
| 4,410,324 | 10/1983 | Sabee . |
| 4,413,996 | 11/1983 | Taylor . |
| 4,480,000 | 10/1984 | Watanabe et al. . |
| 4,501,586 | 2/1985 | Holtman . |
| 4,505,705 | 3/1985 | Matthews et al. . |
| 4,518,451 | 5/1985 | Luceri et al. . |
| 4,531,945 | 7/1985 | Allison . |

(List continued on next page.)

FOREIGN PATENT DOCUMENTS

| | | |
|---|---|---|
| 0062495A2 | 10/1982 | European Pat. Off. . |
| 944242 | 6/1956 | Fed. Rep. of Germany . |
| 389368 | 3/1933 | United Kingdom . |
| 2124907A | 2/1984 | United Kingdom . |

Primary Examiner—C. Fred Rosenbaum
Assistant Examiner—Mark O. Polutta
Attorney, Agent, or Firm—Jeffrey V. Bamber; Steven W. Miller; Richard C. Witte

[57] ABSTRACT

Absorbent articles such as disposable diapers, incontinent pads, sanitary napkins and the like that have multiple layer absorbent cores that are suitable for acquiring and containing liquids in an especially effective and efficient manner. The absorbent core comprises multiple layers including a first layer comprising hydrophilic fibrous material and having an acquisition zone of a relatively lower average density than the other portions of the first layer so that it quickly acquires discharged liquids; a liquid handling layer comprising a resilient material that is moisture insensitive so as to rapidly acquire liquid into itself through the acquisition zone and distribute the liquid throughout the liquid handling layer to a storage layer and the first layer; and a storage layer comprising a combination of fibrous material and discrete particles of absorbent gelling material that contains and stores the liquids deposited onto the absorbent core and allows the liquid handling layer to be ∓drained" of the liquids it has acquired so that the liquid handling layer may have sufficient capacity to acquire and distribute subsequent loadings of liquids.

42 Claims, 3 Drawing Sheets

U.S. PATENT DOCUMENTS

| Patent # | Date | Inventor | Class |
|---|---|---|---|
| 4,540,454 | 9/1985 | Pieniak et al. | |
| 4,551,143 | 11/1985 | Cook et al. | |
| 4,560,372 | 12/1985 | Pieniak | |
| 4,610,678 | 9/1986 | Weisman et al. | |
| 4,623,340 | 11/1986 | Luceri | |
| 4,673,402 | 6/1987 | Weisman et al. | |
| 4,676,784 | 6/1987 | Erdman | 604/368 |
| 4,676,786 | 6/1987 | Nishino | |
| 4,678,464 | 7/1987 | Holtman | |
| 4,699,619 | 10/1987 | Bernardin | 604/378 |
| 4,704,112 | 11/1987 | Suzuki et al. | |
| 4,731,065 | 3/1988 | Yamada | |
| 4,731,071 | 3/1988 | Pigneul | 604/385.1 |
| 4,738,676 | 4/1988 | Osborn, III | |
| 4,781,962 | 11/1988 | Zamarripa et al. | |
| 4,842,594 | 6/1989 | Ness | 604/368 |
| 4,857,065 | 8/1989 | Seal | 604/368 |
| 4,880,419 | 11/1989 | Ness | 604/368 |

ABSORBENT ARTICLES WITH MULTIPLE LAYER ABSORBENT LAYERS

FIELD OF THE INVENTION

This invention relates to absorbent articles, such as disposable diapers, adult incontinent pads, sanitary napkins and the like, having multiple layer absorbent cores. More particularly, the invention relates to an absorbent core having a first layer provided with an acquisition zone, a fluid handling layer for quickly acquiring and distributing liquids into and throughout the absorbent core, and a storage layer for absorbing and retaining such liquids.

BACKGROUND OF THE INVENTION

Absorbent articles such as disposable diapers, adult incontinent pads, sanitary napkins and the like are generally provided with an absorbent core to receive and retain body liquids. In order for such absorbent articles to function efficiently, the absorbent core must quickly acquire body liquids into the structure from the point of application and subsequently distribute the body liquids within and throughout the absorbent core to provide maximum leakage containment. In addition, the absorbent core should be capable of retaining the absorbed liquids when placed under load and have a renewable liquid capacity for acquiring subsequent voids of liquids.

Previous attempts to improve the effectiveness of absorbent cores have included distributing particles of absorbent gelling material throughout or in portions of the absorbent core. For example, U.S. Pat. No. 4,610,678 issued to Paul T. Weisman and Stephen A. Goldman on Sept. 9, 1986, discloses absorbent members wherein particles of absorbent gelling material (hydrogel) are dispersed in an air-laid web of hydrophilic fibrous material and compressed to a particular density. U.S. Pat. No. 4,673,402 issued to Paul T. Weisman, Dawn I. Houghton, and Dale A. Gellert on June 16, 1987, discloses a dual-layer absorbent core wherein an absorbent acquisition/distribution layer overlays a lower fluid storage layer that consists essentially of a uniform combination of hydrophilic fibrous material and discrete particles of absorbent gelling material (hydrogel). European Patent Application EP-A-254,476; The Procter & Gamble Company; published Jan. 27, 1988, discloses absorbent members having a storage zone and an acquisition zone having a lower average density and a lower average basis weight per unit area than the storage zone so that the acquisition zone may effectively and efficiently rapidly acquire discharged liquid.

It has been found that the effectiveness of absorbent gelling material in disposable absorbent articles is quite dependent upon the form, position, and/or manner in which the particles of absorbent gelling material are incorporated into the absorbent core. In some cases, for example, the effectiveness of absorbent cores containing particles of absorbent gelling material can be adversely affected by a phenomenon called "gel blocking." The term gel blocking describes a situation that occurs when a particle of absorbent gelling material is wetted, the surface of the particle swells so as to inhibit liquid transmission into the interior of the absorbent core. Wetting of the interior absorbent core, therefore, takes place via very slow diffusion process. In practical terms, this means that acquisition of liquid by the absorbent core is much slower than the discharge of the liquids to be absorbed, and leakage from the absorbent article may take place well before the particles of absorbent gelling material in the absorbent core are fully saturated or before the liquid can diffuse or wick past the "blocking" particles into the rest of the absorbent core. The slow acquisition rate also fails to take advantage of the rapid wicking of liquids to other parts of the absorbent core provided by a densified absorbent core containing particles of absorbent gelling material.

The structure of the absorbent core may also contribute to leakage of liquids by not providing sufficient capacity for quantities of liquids deposited onto the absorbent core after the initial gush has been deposited onto the absorbent core. Gel blocking and saturation of the materials adjacent the zone of application inhibit acquisition and transmission of these liquids into and throughout the core such that the absorbent core has no additional capacity to absorb these liquids so that there is an increased likelihood of such liquids leaking out of the edges of the absorbent article. Thus, efficient and rapid acquisition and distribution of liquids by and from the initial layers of the core is necessary to insure sufficient capacity for subsequently deposited liquids.

Thus, it would be advantageous to provide an absorbent core that quickly acquires and distributes large quantities of liquids within itself while minimizing gel blocking during the liquid acquisition stage and providing a renewable liquid capacity for acquiring subsequent voids of liquids. It is, therefore, a primary objective of the present invention to provide absorbent cores which are especially effective and efficient in their use of absorbent gelling materials and acquisition/distribution materials.

SUMMARY OF THE INVENTION

The present invention provides absorbent articles such as disposable diapers, incontinent pads, sanitary napkins and the like that have multiple layer absorbent cores that are suitable for acquiring and containing liquids in an especially effective and efficient manner. Such absorbent articles comprise a liquid pervious topsheet, a liquid impervious backsheet joined with the topsheet, and an absorbent core positioned between the topsheet and the backsheet.

The absorbent core comprises multiple layers including a first layer comprising hydrophilic fibrous material and having an acquisition zone of a relatively lower average density than the other portions of the first layer so as to quickly acquire discharged liquids; a liquid handling layer comprising a resilient, low density, high void volume material that is moisture insensitive so as to rapidly acquire liquids into itself through the acquisition zone and distribute the liquids throughout the liquid handling layer to the storage layer and the first layer; and a storage layer comprising a combination of fibrous material and discrete particles of absorbent gelling material that contains and stores the liquids deposited onto the absorbent core and allows the liquid handling layer to be "drained" of the liquids it has acquired so that the liquid handling layer may have sufficient capacity to acquire and distribute subsequent loadings of liquids.

The present invention also relates to multiple layer absorbent cores, per se, of the type heretofore described, which can be employed in absorbent articles. Cores of the type utilized herein in absorbent articles, in addition to providing especially efficient and effective use of absorbent gelling materials, are also especially effective in acquiring, distributing, and storing subsequent loadings of liquids.

BRIEF DESCRIPTION OF THE DRAWINGS

While the specification concludes with claims which particularly point out and distinctly claim the subject matter regarded as forming the present invention, it is believed that the invention will be better understood from the following description taken in conjunction with the accompanying drawings in which:

DETAILED DESCRIPTION OF THE INVENTION

Figure 1:
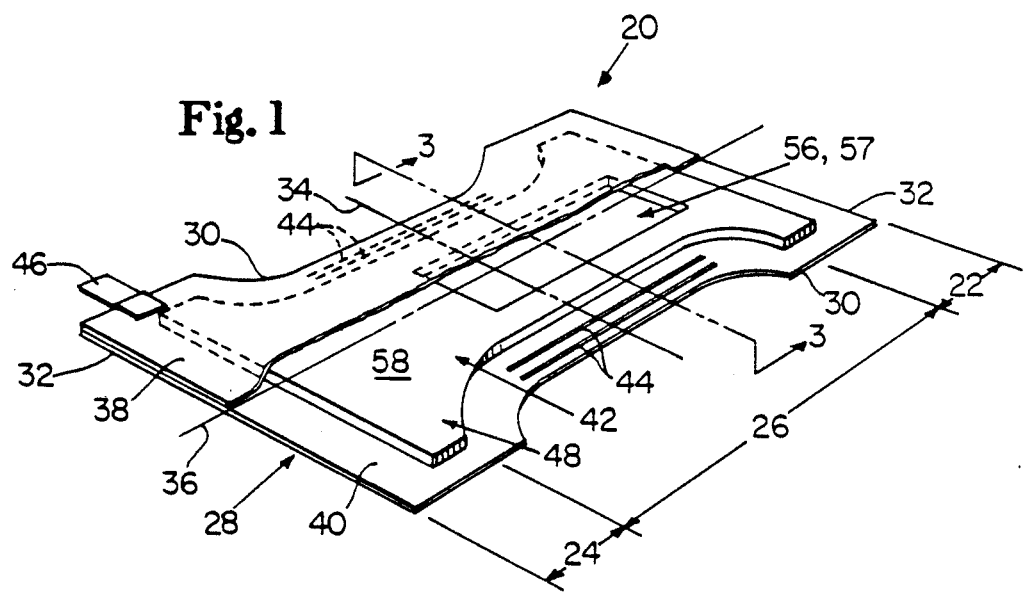
FIG. 1 is a perspective view of a disposable diaper embodiment of the present invention wherein portions of the topsheet and top tissue layer have been cut-away so as to more clearly show the underlying absorbent core of the diaper.

The absorbent cores of the present invention will be described herein in relationship to their use in disposable absorbent articles; however, it should be understood that the potential application of the absorbent cores of the present invention should not be limited to disposable absorbent articles. As used herein, the term "disposable absorbent article" refers to articles which absorb and contain body exudates and, more specifically, refers to articles which are placed against or in proximity to the body of the wearer to absorb and contain the various exudates discharged from the body, and which are intended to be discarded after a single use (i.e., they are not intended to be laundered or otherwise restored or reused). A preferred embodiment of a disposable absorbent article, diaper 20, is shown in FIG. 1. As used herein, the term "diaper" refers to a garment generally worn by infants and incontinent persons that is worn about the lower torso of the wearer. It should be understood, however, that the present invention is also applicable to other disposable absorbent articles such as incontinent briefs, incontinent pads, sanitary napkins and the like.

FIG. 1 is a perspective view of the diaper 20 of the present invention with portions of the structure being cut-away to more clearly show the construction of the diaper 20. The diaper is shown in FIG. 1 to have a front region 22, a back region 24, a crotch region 26, and a periphery 28 which is defined by the outer edges of the diaper in which the longitudinal edges are designated 30 and the end edges are designated 32. The diaper additionally has a transverse centerline 34 and a longitudinal centerline 36.

The diaper 20 comprises a liquid pervious topsheet 38; a liquid impervious backsheet 40; an absorbent core 42; elastic members 44; and tape tab fasteners 46 (only one being shown in FIG. 1). While the topsheet 38, the backsheet 40, the absorbent core 42, and the elastic members 44 may be assembled in a variety of well-known configurations, a preferred diaper configuration is described generally in U.S. Pat. No. 3,860,003 entitled "Contractable Side Portions For Disposable Diaper", which issued to Kenneth B. Buell on Jan. 14, 1975, and which patent is incorporated herein by reference.

FIG. 1 shows a preferred embodiment of the diaper 20 in which the topsheet 38 and the backsheet 40 are co-extensive and have length and width dimensions generally larger than those of the absorbent core 42. The topsheet 38 is joined with and superimposed on the backsheet 40 thereby preferably forming the periphery 28 of the diaper 20. The periphery 28 defines the outer perimeter or the edges of the diaper 20. The periphery 28 comprises the longitudinal edges 30 and the end edges 32.

The diaper 20 has front and back regions 22 and 24, respectively, extending from the end edges 32 of the diaper periphery 28 toward the transverse centerline 34 of the diaper 20 a distance from about 2% to about 20%, preferably about 10%, of the length of the diaper. The front and back regions comprise those portions of the diaper 20, which when worn, encircle the waist of the wearer. The crotch region 26 is that portion of the diaper 20 between the front region 22 and the back region 24, and comprises that portion of the diaper 20 which, when worn, is positioned between the legs of the wearer. Thus, the crotch region 26 defines the area of typical liquid deposition for a diaper 20 or other disposable absorbent article.

Figure 2:
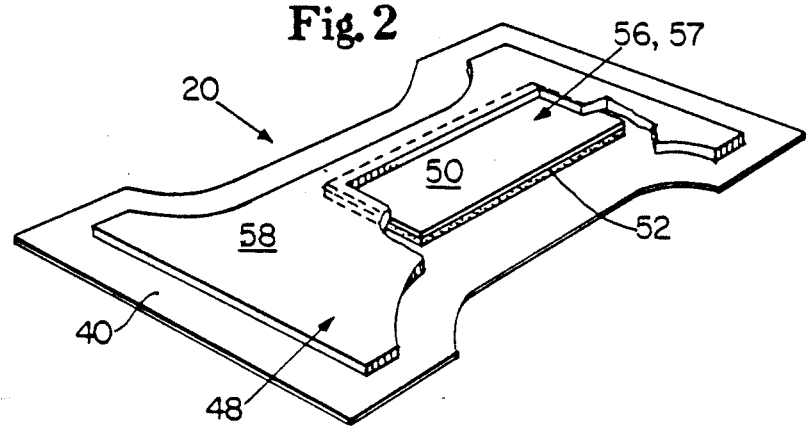
FIG. 2 is a perspective view of the disposable diaper of the present invention wherein the topsheet and the top tissue layer have been removed and the first layer of the absorbent core has been cut-away to more clearly show the underlying liquid handling layer and storage layer of the absorbent core.

FIG. 2 shows the preferred embodiment of the diaper 20 of the present invention, with portions of the diaper 20 removed, so as to more clearly show the absorbent core 42 of the present invention. The absorbent core 42 preferably comprises a first layer 48, a liquid handling layer 50, and a storage layer 52. The first layer 48 has a generally hourglass-shape and has an acquisition zone 56, preferably the rectangular-shaped acquisition aperture 57 as shown in FIG. 2, and a holding zone 58 that at least partially laterally surrounds the perimeter of the acquisition zone 56. The liquid handling layer 50 is the generally rectangular layer positioned subjacent at least the acquisition aperture 57. The storage layer 52 is the generally rectangular layer positioned subjacent the liquid handling layer 50 adjacent the backsheet 40.

Figure 3:
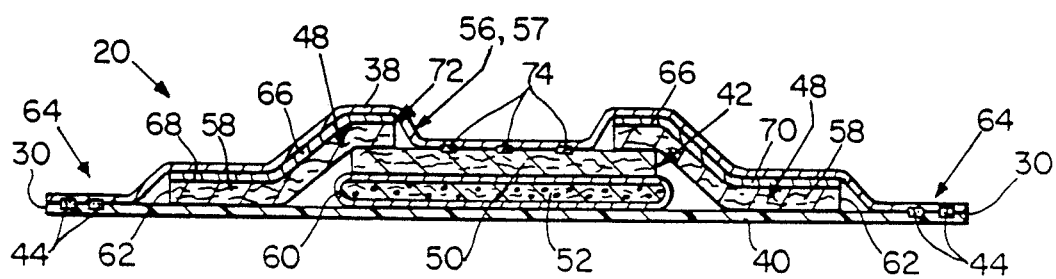
FIG. 3 is a transverse sectional view of the disposable diaper of the present invention taken along section line 3—3 of FIG. 1.

FIG. 3 is a cross-sectional view taken along line 3—3 of FIG. 1 that depicts the diaper construction in the area of typical liquid deposition. The absorbent core 42 comprises the first layer 48 having an acquisition aperture 57 and a holding zone 58, a liquid handling layer 50 positioned subjacent the first layer 48, and a storage layer 52 positioned subjacent the liquid handling layer 50 so as to be positioned between the liquid handling layer 50 and the backsheet 40. The storage layer 52 comprises a combination of fibrous material and discrete particles of absorbent gelling material that is enwrapped by a web 60 of material such as a tissue layer. The absorbent core 42 is positioned between the topsheet 38 and the backsheet 40, both the topsheet 38 and the backsheet 40 preferably extending beyond the side edges 62 of the absorbent core 42 to define side flaps 64. The topsheet 38 and the backsheet 40 also enclose the elastic members 44 adjacent the longitudinal edge 30 in the side flaps 64. A top tissue layer 66 is disposed between the topsheet 38 and the first layer 48 of the absorbent core 42 so as to provide integrity for the first layer 48 during processing and handling of the absorbent core 42. The top tissue layer 66 preferably comprises a first tissue layer 68 and a second tissue layer 70 laterally spaced from each other to provide a tissue acquisition aperture 72 that generally corresponds to the acquisition aperture 57 positioned in the first layer 48 so that liquids deposited onto the topsheet 38 will quickly be acquired into the liquid handling layer 50. The topsheet 38 is also preferably directly joined to the liquid handling layer 50 through the acquisition aperture 57 of the first layer 48 and the tissue acquisition aperture 72 of the top tissue layer 66 by attachment means 74. Since the topsheet 38 is joined directly to the liquid handling layer 50 through the acquisition aperture 57, liquids tend to more quickly pass through the topsheet 38 to the liquid handling layer 50 and have a reduced tendency to pool on the topsheet 38.

The topsheet 38 is compliant, soft feeling, and non-irritating to the wearer's skin. Further, the topsheet 38 is liquid pervious permitting liquids to readily penetrate through its thickness. A suitable topsheet 38 may be manufactured from a wide range of materials, such as porous foams, reticulated foams, apertured plastic films, natural fibers (e.g., wood or cotton fibers), synthetic fibers (e.g., polyester or polypropylene fibers) or from a combination of natural and/or synthetic fibers. Preferably, the topsheet 38 is made of a hydrophobic material to isolate the wearer's skin from liquids in the absorbent core 42.

A particularly preferred topsheet 38 comprises staple length polypropylene fibers having a denier of about 1.5, such as Hercules Type 151 polypropylene marketed by Hercules, Inc. of Wilmington, De. As used herein, the term "staple length fibers" refers to those fibers having a length of about 15.9 mm (0.62 inches).

There are a number of manufacturing techniques which may be used to manufacture the topsheet 38. For example, the topsheet 38 may be woven, non-woven, spunbonded, carded or the like. A preferred topsheet is carded and thermally bonded by means well-known to those skilled in the fabric art. Preferably, the topsheet 38 has a weight from about 18 to about 25 grams per square meter, a minimum dry tensile strength of at least about 400 grams per centimeter in the machine direction and a wet tensile strength of at least about 55 grams per centimeter in the cross-machine direction.

The backsheet 40 is impervious to liquids and is preferably manufactured from a thin plastic film, although other selectable liquid impervious materials may also be used. The backsheet 40 prevents the exudates absorbed and contained in the absorbent core 42 from wetting articles which contact the diaper 20 such as bedsheets and undergarments. Preferably, the backsheet 40 is a polyethylene film having a thickness of from about 0.012 mm (0.5 mil) to about 0.051 cm (2.0 mils), although other flexible, liquid impervious materials may be used. As used herein, the term "flexible" refers to materials which are compliant and which readily conform to the general shape and contours of the wearer's body.

A suitable polyethylene film is manufactured by Monsanto Chemical Corporation and marketed in the trade as Film No. 8020. The backsheet 40 is preferably embossed and/or matte finished to provide a more clothlike appearance. Further, the backsheet 40 may permit vapors to escape from the absorbent core 42 while still preventing exudates from passing through the backsheet 40.

The size of the backsheet 40 is dictated by the size of the absorbent core 42 and the exact diaper design selected. In a preferred embodiment, the backsheet 40 has a modified hourglass-shape extending beyond the absorbent core 42 a minimum distance of at least about 1.3 cm to about 2.5 cm (about 0.5 to about 1.0 inch) around the entire diaper periphery 28.

The topsheet 38 and the backsheet 40 are joined together in any suitable manner. As used herein, the term "joined" encompasses configurations whereby the topsheet 38 is directly secured to the backsheet 40 by affixing the topsheet 38 directly to the backsheet 40, and configurations whereby the topsheet 38 is indirectly secured to the backsheet 40 by affixing the topsheet 38 to intermediate members which in turn are affixed to the backsheet 40. In a preferred embodiment, the topsheet 38 and the backsheet 40 are joined directly to each other in the diaper periphery 28 by attachment means (not shown) such as an adhesive or any other attachment means as known in the art. For example, a uniform continuous layer of adhesive, a patterned layer of adhesive, or an array of separate lines or spots of adhesive may be used to join the topsheet 38 to the backsheet 40.

Tape tab fasteners 46 are typically applied to the back region 24 of the diaper 20 to provide a fastening means for holding the diaper on the wearer. Only one of the tape tab fasteners is shown in FIG. 1. The tape tab fasteners 46 can be any of those well known in the art, such as the fastening tapes disclosed in U.S. Pat. No. 3,848,594 entitled "Tape Fastening System For Disposable Diaper", which issued to Kenneth B. Buell on Nov. 19, 1974, and which patent is incorporated herein by reference. These tape tab fasteners 46 or other diaper fastening means, such as pins, "Velcro" type mechanical fasteners or other fasteners, are typically applied near the corners of the diaper 20.

The elastic members 44 are disposed adjacent the periphery 28 of the diaper 20, preferably along each longitudinal edge 30, so that the elastic members 44 tend to draw and hold the diaper 20 against the legs of the wearer to form leg cuffs. Alternatively, or in addition, elastic members may be disposed adjacent either or both of the end edges 32 of the diaper 20 to provide a waistband (For example, a suitable waistband is disclosed in U.S. Pat. No. 4,515,595 entitled "Disposable Diapers With Elastically Contractible Waistbands", which issued to David J. Kievit and Thomas F. Osterhage on May 7, 1985, and which patent is incorporated herein by reference.) In addition, a method and apparatus suitable for manufacturing a disposable diaper having elastically contractible elastic members is described in U.S. Pat. No. 4,081,301 entitled "Method And Apparatus For Continuously Attaching Discrete, Stretched Elastic Strands To Predetermined Isolated Portions Of Disposable Absorbent Products" which issued to Kenneth B. Buell on March 28, 1978, and which patent is incorporated herein by reference.

The elastic members 44 are secured to the diaper 20 in an elastically contractible condition so that in a normally unrestrained configuration, the elastic members 44 effectively contract or gather the diaper 20. The elastic members 44 can be secured in an elastically contractible condition in at least two ways. For example, the elastic members 44 may be stretched and secured while the diaper 20 is in an uncontracted condition. Alternatively, the diaper 20 may be contracted, for example, by pleating, and the elastic members 44 secured and connected to the diaper 20 while the elastic members 44 are in their unrelaxed or unstretched condition.

In the embodiment illustrated in FIG. 1, the elastic members 44 extend essentially the entire length of the diaper 20 in the crotch region 26. Alternatively, the elastic members 44 may extend the entire length of the diaper 20, or any other length suitable to provide elastically contractible lines. The length of the elastic members 44 is dictated by the diaper's design.

The elastic members 44 may take a multitude of configurations. For example, the width of the elastic members 44 may be varied from about 0.25 mm (0.01 inches) to about 25 mm (1.0 inch) or more; the elastic members 44 may comprise a single strand of elastic material or may comprise several parallel or non-parallel strands of elastic material; or the elastic members 44 may be rectilinear or curvilinear. Still further, the elastic members 44 may be affixed to the diaper in any of several ways which are well-known in the art. For example, the elastic members 44 may be ultrasonically bonded, heat and pressure sealed into the diaper 20 using a variety of bonding patterns, or the elastic members 44 may simply be adhesively secured (e.g., glued) to the diaper 20. An elastic member which has been found to be suitable for use in such a diaper 20 is an elastic tape sold under the tradename Fulflex 9211 by Fulflex Company of Scotland, N.C. Other suitable elastic members may comprise a wide variety of materials as are well known in the art including elastomeric films, polyurethane films, elastromeric foams, formed elastic scrim, and heat shrinkable elastic materials.

The absorbent core 42, which preferably comprises three or more distinct layers, and which is preferably flexible, is positioned between the topsheet 38 and the backsheet 40 to form the diaper 20. The absorbent core 42 is generally compressible, conformable, non-irritating to the wearer's skin, and capable of absorbing and retaining liquids and certain body exudates. The absorbent core 42 essentially comprises a first layer 48, a liquid handling layer 50, and a storage layer 52. It should be understood that for purposes of this invention, these types of layers refer merely to zones of the absorbent core and are not necessarily limited to single layers or sheets of material. Thus, the first layer 48, the liquid handling layer 50, and the storage layer 52 may actually comprise laminates or combinations of several sheets or webs of the requisite type of materials as hereinafter described. Thus, as used herein, the term "layer" includes the term "layers" and "layered."

Figure 4:
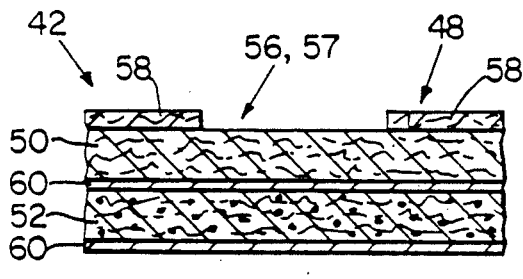
FIG. 4 is a transverse fragmentary sectional view of only the absorbent core of the disposable diaper taken along sectional line 3—3 of FIG. 1.

FIG. 4 shows a fragmentary cross-sectional view of the absorbent core 42 of the present invention. The first layer 48 has an acquisition zone 56, acquisition aperture 57, so as to provide a direct channel to a portion of the liquid handling layer 50, and a holding zone 58 to prevent liquids from passing back through the topsheet 38 onto the skin of the wearer and to absorb liquids. The liquid handling layer 50 is positioned subjacent at least the acquisition zone 56 (acquisition aperture 57) of the first layer 48 so as to acquire liquids deposited onto the absorbent core 42, particularly those that are deposited adjacent the acquisition aperture 57, provide sufficient gush handling capacity for the absorbent core 42, and distribute or transport that liquid in the x-y plane (along its length and width) so that a substantial portion of the liquid is in contact with the top surface of the storage layer 52 and the bottom surface of the first layer 48 at the holding zone 58. The storage layer 52 is positioned subjacent the liquid handling layer 50 so as to pull liquids out of the liquid handling layer 50 and contain and retain those liquids distributed to it by the liquid handling layer 50. As shown in FIG. 4, the storage layer 52 preferably comprises a web or batt comprising a combination of fibrous material and particles of absorbent gelling material, the batt being enwrapped in a web 60 of material such as tissue paper.

One element of the absorbent core 42 is a first layer 48 which preferably comprises a web that comprises essentially hydrophilic fibrous material. This layer serves to prevent already acquired liquids from passing out of the liquid handling layer 50 back through the topsheet 38 and onto the skin of the wearer, to provide a secondary gush capacity for the absorbent core 42, to move liquids away from the topsheet 38, and to collect and to hold discharged liquids deposited onto the holding zone 58 or distributed to the holding zone 58 by either the liquid handling layer 50 or the acquisition zone 56. Since such liquids are generally discharged in gushes, the first layer 48 should also allow rapid acquisition of such liquids from the point of initial contact to other layers of the absorbent core 42. The first layer 48 comprises an acquisition zone 56 and a holding zone 58 in liquid communication with at least a lateral portion of the acquisition zone 56. The acquisition zone 56 preferable comprises the portion of the first layer 48 comprising the acquisition aperture 57 shown FIG. 1. The holding zone 58 generally comprises the remainder of the first layer 48.

Various types of hydrophilic fibrous material can be used in the first layer 48 of the absorbent core 42. Any type of hydrophilic fibers which are suitable for use in conventional absorbent products are also suitable for use in the first layer 48 of the absorbent core 42 of the present invention. Specific examples of preferred hydrophilic fibers include cellulose fibers, rayon, and polyester fibers. Other examples of suitable hydrophilic fibers are hydrophilized hydrophobic fibers, such as surfactant-treated or silica-treated thermoplastic fibers. Also, fibers which do not provide webs of sufficient absorbent capacity to be useful in conventional absorbent structures, but which do provide good wicking properties, are suitable for use in the first layer 48 of the absorbent core 42 of the present invention. This is so because the purpose of the first layer 48 is to acquire and distribute liquid which has passed through the topsheet 38 and to prevent liquids absorbed within the liquid handling layer 50 from rewetting the skin of the wearer. For reasons of availability and cost, cellulose fibers, in particular, wood pulp fibers are preferred.

The first layer 48 of the absorbent core 42 can be substantially free of particles of absorbent gelling material, or can, alternatively, contain small amounts of absorbent gelling material. Thus, it has been found that the first layer 48 can, for example, contain up to about 8%, and preferably up to about 6%, by weight of the first layer 48 of particles of absorbent gelling material. In some instances, the presence of particles of absorbent gelling material in the first layer 48 can serve to maintain the density of the first layer 48 within the optimum range to promote liquid acquisition and distribution. The specific type of absorbent gelling material optionally used in the first layer 48 does not have to be the same as the type essentially employed in the storage layer 52.

The size, shape, and character, including capillarity (e.g., pore size or density and basis weight) of the first layer 48 has some importance in determining the effectiveness of the resulting absorbent cores in absorbing discharged body liquids. As shown in FIG. 1, the first layer 48 is preferably hourglass-shaped. The first layer 48 can alternatively be of any desired shape, for example, rectangular, trapezoidal, oval, or oblong. The shape of the first layer 48 of the absorbent core 42 will frequently define the general shape of the resulting diaper or absorbent article.

It has been found that a relative capillarity difference between the acquisition zone 56 and the holding zone 58 is of importance in the overall efficiency and effectiveness of the first layer 48. While liquid capillarity can be defined in several ways (e.g., pore size, density, basis weight, etc.), the density and basis weight of the structure are the preferred parameters to define liquid capillarity in the first layer 48 of the present invention. Thus, the acquisition zone 56 should have both a relatively lower average density and lower average basis weight per unit area than the holding zone 58 to establish the preferred capillarity force gradient between them. Thus, the acquisition zone 56 can comprise an aperture of zero density and basis weight or an area wherein the ratio of the average density of the holding zone 58 to the average density of the acquisition zone 56 should preferably be at least about 1.25:1, more preferably at least about 1.5:1, and most preferably at least about 2:1.

The holding zone 58 is the relatively higher capillarity (higher density and basis weight per unit area) portion of the first layer 48. The primary functions of the holding zone 58 are to absorb discharged liquids that are either deposited directly onto the holding zone 58 or transferred to the holding zone 58 via the capillary force gradient established between the acquisition zone 56 and the holding zone 58 or between the liquid handling layer 50 and the holding zone 58, and to prevent liquids acquired by the absorbent core 42 from passing back through the topsheet 38 and onto the skin of the wearer. Preferably, the holding zone 58 consists essentially of the structure of the upper liquid acquisition/distribution layer disclosed in the above-referenced U.S. Pat. No. 4,673,402, entitled "Absorbent Articles With Dual-Layered Cores" which issued to Weisman et al. on June 16, 1987, which is incorporated herein by reference, although other structures may also be used.

The holding zone 58 preferably has a relatively higher density and a higher basis weight per unit area than the acquisition zone 56. The density and basis weight values of the holding zone 58 include the weight of the particles of absorbent gelling material, such that the density and basis weight values will vary depending upon the amount of particles dispersed throughout the first layer 48. Thus, the holding zone 58 will generally have a density of from about 0.05 to about 0.25 g/cm$^3$, and more preferably within the range of from about 0.07 to about 0.14 g/cm$^3$, wherein the first layer 48 contains up to about 8% by weight of particles of absorbent gelling material. The basis weight of such a holding zone 58 can range from about 0.015 to about 0.1 g/cm$^2$, preferably from about 0.03 to about 0.06 g/cm$^2$. The density of the holding zone 58 is calculated from its basis weight and caliper measured on newly unpacked, unfolded, and dissected diapers. The caliper is measured using a standard gauge with a sample under a load of 0.1 psi. The basis weight is measured by die-cutting a certain size sample and weighing this sample on a standard scale, the weight and area of the sample determining the basis weight. (It should be noted that the density and basis weight values include the weight of the particles of absorbent gelling material).

While the holding zone 58 may take on a number of sizes and shapes, it is preferred that the holding zone 58 comprises the remainder of the first layer 48 (i.e., the portion of the first layer 48 wherein there is no acquisition zone 56). While certain portions of the first layer 48 need not comprise the holding zone 58, in a particularly preferred embodiment of the absorbent core 42 shown in FIGS. 1-4, the entire first layer 48 except for the acquisition zone 56 consists of the holding zone 58. In addition, while the holding zone 58 need not completely laterally surround the acquisition zone 56 (i.e., it is in liquid communication with at least a portion of the lateral area of the acquisition zone 56), in preferred embodiments of the present invention, the holding zone 58 laterally surrounds the acquisition zone 56.

The acquisition zone 56 has a relatively lower capillarity and thus preferably a lower average density and a lower average basis weight per unit area than the holding zone 58. The acquisition zone 56 serves to collect and to distribute to the liquid handling layer 50 and to the holding zone 58 reasonably large amounts of discharged liquid. Since such liquids are generally discharged in gushes, the acquisition zone 56 must be able to quickly acquire and transport liquid from the point of liquid contact to other parts of the absorbent core 42, preferably to the liquid handling layer 50, with a minimum of liquid flow resistance. The acquisition zone 56 preferably comprises the acquisition aperture 57 shown in FIGS. 1-4. The acquisition zone 56 thus preferably has a density of 0.0 g/cm$^3$ (an acquisition aperture) although it may also vary from about 0.03 g/cm$^3$ to about 0.24 g/cm$^3$ The basis weight of such an acquisition zone 56 will preferably be 0.0 g/cm$^2$ or alternatively range from about 0.05 g/cm$^2$ to about 0.1 g/cm.2 The density of the acquisition zone 56 is calculated from its basis weight and caliper measured on newly unpacked, unfolded, and dissected diapers. The caliper is measured using a standard gauge with a sample under a load of 0.1 psi. The basis weight is measured by die-cutting a certain size sample and weighing the sample on a standard scale, the weight and the area of the sample determining the basis weight. (The density and basis weight values include the weight of the particles of absorbent gelling material.)

The shape, size, and positioning of the acquisition zone 56 is of importance in determining the effectiveness of the resulting absorbent core 42 in rapidly acquiring discharged liquids. In accordance with the present invention, the acquisition zone 56 should be placed in a specific positional relationship with respect to the area of typical liquid deposition of the absorbent core 42. While portions of the acquisition zone 56 may be positioned anywhere in the first layer 48, the acquisition zone 56 is preferably positioned generally in the front two-thirds portion of the first layer 48 so that the acquisition zone 56 is positioned in the area of typical liquid deposition, (i.e., the deposition region). Thus, the acquisition zone 56 is placed in the vicinity of the point of discharge of liquids so as to be capable of quickly acquiring such liquids at their contact zone.

The generally forward positioning of the acquisition zone 56 can be defined by specifying the percentage of the volume or top surface area of the acquisition zone 56 which is found forward of particular points along the length of the first layer 48. While the positioning of the acquisition zone 56 can be defined with respect to the volume of the acquisition zone 56 positioned forward of particular points, it has been found that the top surface area of the acquisition zone 56 is a more desirable definition because the top surface area actually defines the initial area available for liquid acquisition. In addition, since the thickness of the first layer 48 is preferably uniform and the acquisition zone 56 has a generally rectangular cross-sectional area, the top surface area definition is equal to a volumetric definition in a preferred embodiment. Thus, the positioning of the acquisition zone 56 will be referenced throughout the specification as related to its top surface area. (i.e., the percentage of the top surface area of the acquisition zone positioned in a given area.)

Thus, in accordance with the present invention, at least a portion of the acquisition zone 56 must be placed in the area of typical liquid deposition, even though remaining portions may be positioned anywhere in the first layer 48. (It should be understood that if plural acquisition zones are utilized, at least a portion of one of the acquisition zones must be positioned in the area of typical liquid deposition.) Thus, at least about 75% of the top surface area of the acquisition zone 56 is positioned in the front three-fourths, preferably the front two-thirds, section of the first layer 48. The acquisition zone 56 is preferably positioned relative to the first layer 48 such that the top surface area of the acquisition zone 56 is completely (100%) positioned within the front three-quarters section of the first layer 48, more preferably the front two-thirds section, and most preferably between the front 10% and 60% of the first layer 48. The acquisition zone 56 is also preferably centered about the longitudinal centerline 36 of the diaper 20.

The forward positioning of the acquisition zone 56 may alternatively be defined by specifying the percentage of the top surface area of the acquisition zone 56 that is found forward of particular points along the length of the diaper 20 or other absorbent article. Thus, the acquisition zone 56 is preferably positioned on the first layer 48 relative to the backsheet 40 such that at least a portion, preferably at least about 75%, of the top surface area of the acquisition zone is in the crotch region 26 of the diaper 20. More preferably, the acquisition zone 56 is positioned such that its top surface area is completely (100%) positioned in the crotch region 26 and the front region 22 of the diaper 20, most preferably in the crotch region 26.

The acquisition zone 56 can be of any desired shape consistent with the absorbency requirements of the absorbent core 42 or the diaper 20 including, for example, circular, rectangular, triangular, trapezoidal, oblong, hourglass-shaped, funnel-shaped, dogbone-shaped, fox-shaped, or oval. Preferred shapes of the acquisition zone 56 are those that increase the perimeter of the lateral interface between the acquisition zone 56 and the holding zone 58 so that the relative capillarity difference between the zones are fully utilized. In a preferred embodiment as shown in FIGS. 1 and 2, the acquisition zone 56 will be a rectangular-shaped acquisition aperture 57 having a top surface area of about 56.5 $cm^2$ (8.75 $in^2$) so that the top surface area of the acquisition aperture 57 comprises about 10% of the total surface area (including the top surface area of the acquisition zone 56) of the first layer 48 for a medium size diaper.

In order to maintain a certain minimal absorbency level in the first layer 48 and reduce the wetback of liquids through the topsheet 38, the top surface area or volume of the holding zone 58 must comprise some minimal amount of the top surface area or volume of the first layer 48. Thus, it has been found that the acquisition zone 56 should preferably comprise less than the total top surface area and/or volume of the first layer 48. The top surface area of the acquisition zone 56 preferably comprises less than about 50% of the total top surface area of the first layer 48. More preferably, the top surface area of the acquisition zone 56 comprises less than about 35% of the total top surface area of the first layer 48, with less than about 20% being especially preferred.

The acquisition zone 56 may also have a number of different cross-sectional areas and configurations including those wherein the area of portions of the acquisition zone in planes below the top plane of the first layer 48 is less than or greater than its top surface area (i.e., the acquisition zone 56 is smaller or wider below the top surface of the first layer 48.) For example, the acquisition zone 56 may have conical, trapezoidal, T-shaped, or rectangular cross-sectional areas. As shown in FIG. 3, the acquisition zone 56 preferably has a rectangular cross-sectional area.

Figure 10:
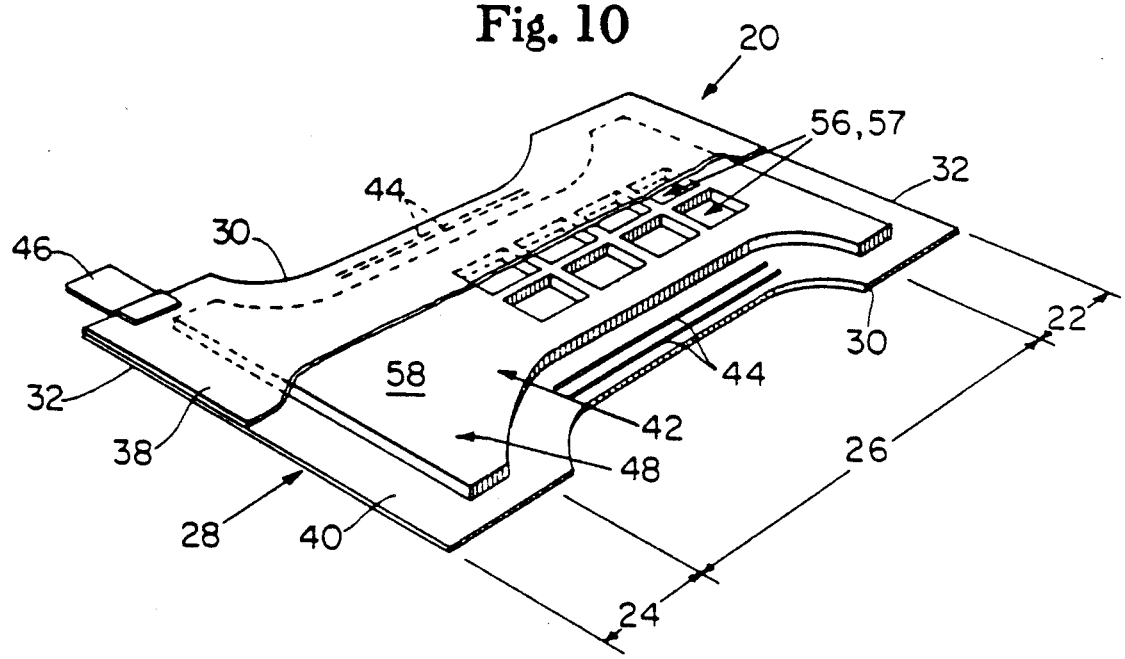
FIG. 10 is a perspective view of a disposable diaper embodiment of the present invention showing multiple acquisition apertures, wherein portions of the topsheet and top tissue layer have been cut-away to more clearly show the underlying absorbent core of the diaper.

As shown in FIG. 10, the acquisition zone 56 of the present invention preferably comprises one or more acquisition apertures so that a portion of the liquid handling layer 50 is positioned immediately subjacent the topsheet 38. An acquisition aperture 57 provides the lowest density and basis weight acquisition zone 56. An acquisition aperture 57 also preferably provides improved rates of liquid acquisition because there is reduced interference to liquid flow. Therefore, gushes of liquids will readily and easily pass through the topsheet 38 and the acquisition aperture 57 and onto the liquid handling layer 50 without having an opportunity to flow along the surface of the topsheet 38. As shown in FIG. 3, the topsheet 38 is preferably secured to the liquid handling layer 50 through the acquisition aperture 57 by attachment means 74 to provide intimate contact between the liquid handling layer 50 and the topsheet 38 so that liquids will not pool or collect on the topsheet 38 but be acquired into the liquid handling layer 50.

While the acquisition zone 56 preferably comprises an acquisition aperture 57, the acquisition zone 56 may alternatively have some fibers or other absorbent material so as to have a density and basis weight per unit area greater than zero. Such an acquisition zone would typically comprise the same material as the material that comprises the holding zone 58 (preferably hydrophilic fibrous material and from 0% to about 8%, by weight, of particles of absorbent gelling material) such as the absorbent member described generally in EP-A 254,476; The Procter & Gamble Company, published Jan. 27, 1988, which is incorporated herein by reference.

Figure 9:
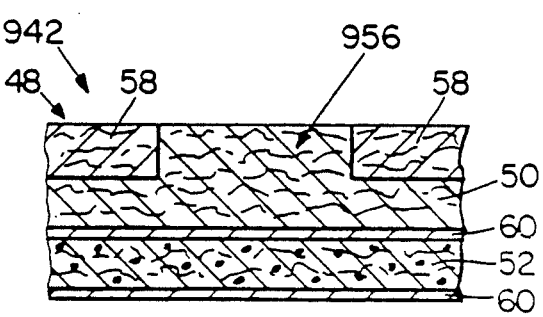
FIG. 9 is a fragmentary sectional view of an even still further alternative embodiment of the absorbent core of the present invention.

Alternatively, however, the acquisition zone 56 may comprise a different material than the holding zone 58. For example, the acquisition zone 56 may comprise any material suitable for use in an absorbent core 42 that has a lower capillarity, preferably a lower average density and a lower average basis weight per unit area, than the holding zone 58. If the acquisition zone 56 comprises a different material than the holding zone 58, it is preferable that the acquisition zone 56 comprise the same material as used in the liquid handling layer 50. Since the acquisition zone 56 can comprise the same material as the liquid handling layer 50, the acquisition zone 56 may comprise a separate piece or batt of material incorporated into the first layer 48 or it could be unitary (the same layer) with the liquid handling layer 50 so that the batt of material would form both the acquisition zone 56 of the first layer 48 and the liquid handling layer 50. (It should be noted that after processing and handling of the diaper 20 shown in FIGS. 1-4, the absorbent core 42 generally will have been compressed such that the portion of the liquid handling layer 50 positioned immediately subjacent the acquisition aperture 57 will expand into the acquisition aperture 57 such that the acquisition zone 56 appears to be formed as a unitary portion of the liquid handling layer 50 (such as shown in FIG. 9) rather than as an acquisition aperture 57.)

The second component of the absorbent core 42 of the present invention is the liquid handling layer 50. The liquid handling layer 50 serves to quickly collect and transport discharged body liquids into and throughout itself and to other portions of the absorbent core 42. Since such liquids are discharged in gushes, the liquid handling layer 50 must have some gush handling capacity so as to allow liquids to freely and quickly move into the liquid handling layer 50 and the ability to transport liquids either by hydraulic transport or capillary flow from the point of initial contact on the liquid handling layer 50 to other parts of the liquid handling layer 50 and the absorbent core 42. The liquid handling layer 50 also preferably provides a member that contains and quickly acquires subsequent gushes of liquid.

The liquid handling layer 50 must have some gush handling capacity so that the liquid handling layer 50 can rapidly receive practical quantities of liquids and other body exudates. The gush handling capacity of the liquid handling layer 50 is related to the void volume of the structure of the liquid handling layer 50. The liquid handling layer 50 should, therefore, be manufactured of a material that has sufficient void volume in the interstices or capillaries between the material or fibers to contain practical quantities of liquid. Void volume within the liquid handling layer 50 serves as a reservoir or "bucket" for large gushes of liquid with a minimum resistance to flow within the structure so that the liquid handling layer 50 may acquire and transport rapidly voided body liquids.

It has been found that the liquid handling layer 50 should have a percentage void volume greater than about 80%, preferably greater than about 90% (typically between about 93% and 99%), so that there is sufficient void volume to contain in-use quantities of liquids or body exudates. The percentage void volume is calculated by the equation:

$$\text{Percentage void volume} = (1 - V_m/V_s) \times 100\%$$

wherein $V_m$ is the volume of the material determined by dividing the weight of the material or fibers in a given sample by the density of the material or fibers, and wherein $V_s$ is the volume of the sample calculated by multiplying its area times its caliper measured under a load of 0.1 psi. Preferably, the liquid handling layer 50 has a void volume of at least about 5 cm$^3$, more preferably at least about 10 cm$^3$, and most preferably at least about 15 cm$^3$ (In an especially preferred embodiment, the liquid handling layer 50 has a void volume of about 26.4 cm$^3$.)

In order to provide a liquid handling layer 50 that maintains its void volume when placed into a diaper so that the liquid handling layer 50 is especially effective in acquiring initial and subsequent gushes of liquid, the liquid handling layer 50 should be resilient. The liquid handling layer 50 should be resilient so that it must, without the application of external forces, return to essentially its original size and shape after the forces which are applied to it are removed. Preferably, the material used in manufacturing the liquid handling layer 50 possesses such resiliency that it will recover at least about 80% of its original volume after it is compressed to about 20% of its original volume when the compressing forces are removed. Most preferably, the material will recover at least about 90% of its original volume after it is compressed to about 50% of its original volume when the compressing forces are removed.

Because the absorbent core 42 needs to be able to acquire subsequent gushes of liquid deposited onto it, the liquid handling layer 50 should also be essentially unaffected by the presence of liquids such as urine; that is to say, the liquid handling layer 50 should possess a high degree of wet resiliency. The liquid handling layer 50 should retain sufficient inherent resiliency, even when wet, to impart to the liquid handling layer 50 sufficient resiliency to resist close packing of the absorbent material or fibers and retention of the characteristics of the "springy" three dimensional structure so that the liquid handling layer 50 will maintain its void volume and ability to contain gushes of liquid subsequently deposited onto the liquid handling layer 50. Certain materials and fibers, such as rayon or cellulose fibers, have a high degree of resiliency in the dry state, but are essentially non-resilient when wetted. Such materials and fibers are, in general, not useful in the present invention as a liquid handling layer 50. The term "moisture insensitive" is used herein to describe materials and fibers whose resiliency is relatively unaffected by the presence of moisture (wet resilient).

The liquid handling layer 50 also must allow the liquids to quickly penetrate into itself and transport those liquids to other portions of the liquid handling layer 50 and eventually to the storage layer 52 and the holding zone 58 of the first layer 48. The liquid handling layer 50 should thus, it is believed, have low resistance to flow of liquids into and throughout the structure, a high permeability to allow liquids to be hydraulically transported into and throughout the liquid handling layer 50, and a low capillarity to allow capillary flow within the structure and enhance liquid transfer from the liquid handling layer 50 to the storage layer 52 and the holding zone 58. Thus, the liquid handling layer 50 should preferably have a relatively lower capillarity (e.g., larger pore size or lower average density and/or basis weight per unit area) than the storage layer 52 and the holding zone 58 of the first layer 48 so that liquids are transferred to the storage layer 52 and the holding zone 58 wherein the liquids are contained and stored.

Preferably, the liquid handling layer 50 comprises a mass or batt of synthetic fibers. While the liquid handling layer 50 can comprise other materials, such as synthetic foam materials or resilient polymeric foams, the use of such materials is less preferred than the use of a fibrous batt.

Synthetic fibers useful in the present invention include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Especially preferred fibers are polyester fibers. Preferred fibers have a denier of from about 3 denier per filament to about 25 denier per filament, most preferably from about 5 denier per filament to about 16 denier per filament.

The batt of fibers is preferably formed of hydrophobic fibers of a synthetic material because these types of materials exhibit an inherent dry and wet resilience. Other materials may also be used as long as the fibers exhibit dry and wet resilience. For example, fibers that are bonded together at their point of intersection usually exhibit the necessary wet and dry resilience. As indicated herein, the resiliency of the liquid handling layer 50 can frequently be enhanced if the fibers are bonded together at their points of contact. Thus, the material will have a higher resistance to compression such that the void volume of the material will be maintained even under load. Thermal bonding, resin bonding, heat-through bonding, powder bonding, chemical bonding or adhesive bonding can be used to bond the synthetic fibers one to another.

Since the preferred fibers are hydrophobic and will not absorb liquids into their interiors, the surfaces of the fibers are also hydrophobic. Therefore, in order for the interstices of the batt of fibers to more easily acquire sufficient quantities of liquids into the structure of the liquid handling layer 50, the surfaces of the fibers can be rendered hydrophilic. More generally, the liquid handling layer 50 can comprise a material having interstices or capillaries which are wetted by the liquids in question. Urine and other body liquids are primary liquid aqueous solutions and suspensions; surfaces which are wetted by these liquids can be broadly described as hydrophilic. As used in this specification, the term "hydrophilic" describes surfaces which are wetted by the liquid in question. The state of the art respecting wetting of materials allows a definition of hydrophilicity (and wetting) in terms of contact angles and the surface tension of the liquids and solids involved. This is discussed in detail in The American Chemical Society Publication entitled, Contact Angle, Wettability, and Adhesion, edited by Robert F. Gould and copyrighted in 1964, which publication is incorporated herein by reference. A surface is said to be wetted by a liquid either when the contact angle between the liquid and the surface is less than 90° or when the liquid will tend to spread spontaneously across the surface; both conditions normally coexisting.

The materials used in the liquid handling layer 50 can achieve hydrophilicity by any convenient means. For example, the material itself can be extrinsicly hydrophilic, although as discussed herein, this circumstance is relatively rare for materials useful in the liquid handling layer 50. The surfaces of the liquid handling layer 50 can be rendered hydrophilic by treatment with a surfactant, such as a non-ionic or anionic surfactant, as by spraying the material with a surfactant or by dipping the material into the surfactant. By treating the surfaces of the fibers with a surfactant, only the surfaces of the fibers exhibit hydrophilic characteristics while the fiber itself remains hydrophobic. Suitable surfactants include non-ionic surfactants such as Brij 76 manufactured by ICI Americas, Inc. of Wilmington, De. and the various materials sold under the Pegosperse trademark by Glyco Chemical, Inc. of Greenwich, Conn. Anionic surfactants can also be used. Surfactants are applied to the fibers at a level of from about 0.2 to about 1 gram per square meter of material.

In order to maintain a high void volume and a high level of liquid transport, it is believed that the batt of synthetic fibers of the liquid handling layer 50 should have a caliper, measured under a load of 0.1 psi, of greater than about 0.25 mm (0.01 inches), preferably greater than about 0.38 mm (0.015 inches), more preferably greater than about 0.5 mm (0.02 inches), and most preferably greater than about 0.63 mm (0.025 inches). The basis weight of the batt of fibers is preferably about 15 to about 75 g/yd$^2$, most preferably about 20 to about 30 g/yd$^2$.

A most preferred execution of the liquid handling layer 50 comprises a batt of polyester fibers such as Kodel type 435 polyester fibers that are powder bonded into an open structure. The fibers have a denier of about 5.5 denier per filament, a basis weight of about 30 grams per square yard, a caliper under load at 0.1 psi of about 0.68 mm (0.027 inches) and a percentage void volume of about 96%. Such a batt is manufactured by the Eastman Chemical Company of Kingsport, Tennessee. Alternatively preferred examples include batts of polyester fibers that are chemically bonded, have a denier of about 6 denier per fiber and a basis weight of 30 grams per square yard; or that are powder bonded, have a denier of about 15 denier per fiber, and a basis weight of 75 grams per square yard. Other examples of suitable batts of fibers useful in the present invention are found in U.S. Pat. No. 4,738,676 entitled "Pantiliner" which issued to Thomas W. Osborn, III, on April 19, 1988, which is incorporated herein by reference.

Synthetic foams useful as the liquid handling layer 50 include polyester foam materials (such as those described in U.S. Pat. No. 4,110,276 issued to DeMarais on Aug. 29, 1978, and incorporated herein by reference), polyurethane foams, styrene-butadiene foams, resilient polymeric foams, and cellulose sponge material. Synthetic foams should be soft, flexible and open-celled. Its interior surfaces are preferably hydrophilic. Incorporation of surfactant during foam manufacture or addition of surfactants to the preformed foam are two suitable methods of insuring that the interior surfaces are hydrophilic.

The liquid handling layer 50 of the absorbent core 42 need not be the same size as the first layer 48 of the absorbent core 42 and preferably has a top surface area which is substantially smaller than the top surface area of the first layer 48 (including the top surface area of the acquisition aperture 57). Generally, the top surface area of the liquid handling layer 50 will be not less than the surface area of the acquisition zone 56 or acquisition aperture 57 of the first layer 48. Most preferably, the top surface area of the liquid handling layer 50 will be from about 0.1 to 1.0, more preferably from about 0.2 to about 0.75, and most preferably from about 0.25 to about 0.5, times the total top surface area of the first layer 48.

The liquid handling layer 50 of the absorbent core 42 should be placed in a specific positional relationship with respect to the acquisition zone 56 and/or the storage layer 52 in the diaper 20. More particularly, the liquid handling layer 50 of the absorbent core 42 should be positioned at least subjacent the acquisition zone 56 (acquisition aperture 57) of the first layer 48 so that the liquid handling layer 50 is most effectively located to quickly acquire and distribute discharged body liquid deposited onto the absorbent core 42. Thus, the liquid handling layer 50 is placed generally in the vicinity of the point of discharge of body liquids.

The positioning of the liquid handling layer 50 also preferably coincides with the positioning of the storage layer 52. Since the liquid handling layer 50 quickly and efficiently transports liquids to the storage layer 52, it is most preferable that the storage layer 52 be positioned subjacent the liquid handling layer 50. Thus, the liquid handling layer 50 and the storage layer 52 are positioned generally in the same regions of the diaper 20, as defined hereinafter, so that liquids can be efficiently acquired through the acquisition zone 56 of the first layer 48 into the liquid handling layer 50 and onto the storage layer 52.

While the liquid handling layer 50 of the absorbent core 42 can be as large as or larger than the storage layer 52 of the absorbent core 42, the liquid handling layer 50 need not be as large as the storage layer 52 of the absorbent core 42 and can have a top surface area which is slightly less than the top surface area of the storage layer 52 of the absorbent core 42. Generally, the top surface area of the liquid handling layer 50 will range from about 0.75 to about 1.25 times the top surface area of the storage layer 52. More preferably, the top surface area of the liquid handling layer 50 will be from about 0.80 to about 1.0 times that of the storage layer 52. The liquid handling layer 50 is preferably smaller in surface area than the storage layer 52 so that liquids are not wicked beyond the edges of the storage layer 52 where they would not be adequately contained by the storage layer 52. Thus, the liquid handling layer 50 is preferably smaller in surface area than the storage layer 52 as shown in FIG. 3.

The liquid handling layer 50 of the absorbent core 42 can be of any desired shape consistent with comfortable fit including, for example, circular, rectangular, trapezoidal, oblong, hourglass-shaped, dogbone-shaped, or oval. The liquid handling layer 50 need not be physically separated from the first layer 48 or the storage layer 52 or both and can simply form a zone in a continuous web of material. More preferably, however, the liquid handling layer 50 will comprise a separate web which can be used as an insert positioned subjacent the acquisition zone 56 of the first layer 48. In preferred embodiments, the liquid handling layer 50 will be rectangular.

The storage layer 52 of the absorbent core 42 of the diaper herein preferably comprises a combination of hydrophilic fibrous material and discrete particles of absorbent gelling material. The principal function of the storage layer 52 is to absorb discharged body liquids from the liquid handling layer 50 and retain such liquids under the pressures encountered as a result of the wearer's movement. Ideally, the storage layer 52 will drain the fluid handling layer 50 of much of its acquired liquid load.

The hydrophilic fibers in the storage layer 52 can be of the same type as those hereinbefore described for use in the first layer 48. As in the first layer 48, cellulose fibers, and especially wood pulp fibers, are preferred.

In addition to hydrophilic fibrous material, the storage layer 52 also contains discrete particles of absorbent gelling material. Such absorbent gelling materials are inorganic or organic compounds capable of absorbing liquids and retaining them under moderate pressures.

Suitable absorbent gelling materials can be inorganic materials such as silica gels or organic compounds such as cross-linked polymers. Cross-linking may be by covalent, ionic, van der Walls, or hydrogen bonding. Examples of absorbent gelling material polymers include polyacrylamides, polyvinyl alcohol, ethylene-maleic anhydride copolymers, polyvinyl ethers, hydroxypropyl cellulose, carboxymethyl cellulose, polyvinyl morpholine, polymers and copolymers of vinyl sulfonic acid, polyacrylates, polyacrylamides, polyvinyl paradene and the like. Suitable absorbent gelling materials are disclosed in U.S. Pat. No. 3,901,236 entitled "Disposable Absorbent Articles Containing Hydrogel Composites Having Improved Fluid Absorption Efficiencies And Processes For Preparation" issued to Assarson et al. on Aug. 26, 1975, and in U.S. Pat. Re. 32,649 entitled "Hydrogel-Forming Polymer Compositions For Use In Absorbent Structures" issued to Kerryn A. Brandt, Stephen A. Goldman and Thomas A. Inglin on April 19, 1988, both of which are incorporated herein by reference. Preferred polymers for use in the absorbent core include hydrolized acrylonitrile grafted starch, acrylic acid grafted starch, polyacrylate and maleic anhydride copolymers, or mixtures thereof.

The relative amount of hydrophilic fibrous material and particles of absorbent gelling material used in the storage layer 52 can be most conveniently expressed in terms of a weight percentage of the storage layer 52. The storage layer 52 preferably contains from about 2% to about 60%, more preferably from about 9% to about 50%, and most preferably from about 10% to about 25%, by weight, of the storage layer 52 of particles of absorbent gelling material. This concentration of absorbent gelling material can also be expressed in terms of a weight ratio of fiber to particulate. These ratios may range from about 40:60 to about 98:2 or from about 75:25 to about 90:10. For most commercially available absorbent gelling materials, the optimum fiber-to-particulate weight ratio is in the range of from about 50:50 to about 91:9.

In addition, the particles of absorbent gelling material may be dispersed in various ratios throughout different regions and thicknesses of the storage layer 52. For example, the combination of hydrophilic fibrous material and particles of absorbent gelling material may be disposed only in certain portions of the storage layer 52. The storage layer 52 preferably contains an intimate admixture of hydrophilic fibrous material and discrete particles of absorbent gelling material. It is most preferred that the particles are substantially uniformly distributed throughout the entire storage layer 52.

Alternatively, the storage layer 52 can comprise a laminate of particles of absorbent gelling material overwrapped with webs of fibrous material such as tissue paper. Such a laminate structure is more fully described in U.S. Pat. No. 4,578,068 entitled "Absorbent Laminate Structure" issued to Timothy A. Kramer, Gerald A. Young, and Ronald W. Kock on March 25, 1986, which patent is incorporated herein by reference.

The storage layer 52 of the absorbent core 42 need not be as large as the first layer 48 of the absorbent core 42 and can, in fact, have a top surface area which is substantially less than the top surface area (including the surface area of the acquisition aperture 57) of the first layer 48 of the absorbent core 42. The storage layer 52 preferably has a top surface area not less than the surface area of the acquisition zone 56. Generally, the top surface area of the storage layer 52 will range from about 0.10 to 1.0 times that of the first layer 48. More preferably, the top surface area of the storage layer 52 will be only from about 0.2 to about 0.75, and most preferably from about 0.25 to about 0.5, times that of the first layer 48.

The storage layer 52 of the absorbent core 42 can be of any desired shape consistent with comfortable fit including, for example, circular, rectangular, trapezoidal, oblong, hourglass-shaped, dog-bone-shaped, or oval.

The storage layer 52 need not be physically separated from the first layer 48, the liquid handling layer 50, or both and can simply form a zone of high absorbent gelling material concentration in a continuous web of material. More preferably, however, the storage layer 52 of the absorbent core 42 will comprise a separate web which is positioned subjacent the first layer 48 and the liquid handling layer 50, preferably between the liquid handling layer 50 and the backsheet 40.

If desired, the storage layer 52 can be wrapped in an envelope web 60 such as tissue paper or a synthetic core, (e.g., non-woven material) to minimize the potential for particles of absorbent gelling material to migrate out of the storage layer 52. Another objective of such overwrapping is to desirably increase the in-use integrity of the absorbent core 42. Such a web can, in fact, be glued to the storage layer 52. Suitable means for carrying out this gluing operation include the glue-spraying procedure described in U.S. Pat. No. 4,573,986 entitled "Disposable Waste-Containment Garment", which issued to James A. Minetola and David R. Tucker on March 4, 1986, which patent is incorporated herein by reference. Alternatively, the storage layer 52 may be wrapped in a material similiar to the material used for the liquid handling layer 50 so that liquids may be transported to other surfaces of the storage layer 52.

In preferred embodiments, the storage layer 52 of the absorbent core 42 will be rectangular. In especially preferred embodiments such as shown in FIGS. 3 and 4, the rectangular storage layer 52 is overwrapped with an envelope web 60 of material such as tissue paper that is spray-glued to the storage layer 52.

Referring again to FIG. 3 which illustrates a preferred embodiment of the present invention, a top tissue layer 66 is interposed between the topsheet 38 and the first layer 48 of the absorbent core 42. Any material which increases the tensile strength of the first layer 48 can be used as the top tissue layer 66. Preferably, the top tissue layer 66 comprises a sheet or sheets of tissue paper closely associated with the inner surface of the topsheet 38. Tissue papers used in commonly available facial tissue products, such as that marketed under the registered trademark PUFFS by The Procter & Gamble Company of Cincinnati, Ohio can be used. Especially preferred are tissue papers manufactured by either of the processes described in U.S. Pat. No. 3,301,746 issued to Sanford and Assarsson on Jan. 31, 1967 and U.S. Pat. No. 3,994,771 issued to Morgan and Rich on Nov. 30, 1976. Both of these patents are incorporated herein by reference. The top tissue layer 66 preferably does not overlie the acquisition zone 56 of the first layer 48 so that liquids may readily penetrate the topsheet 38 into the liquid handling layer 50 through the acquisition aperture 57 or acquisition zone 56 of the first layer 48. Thus, if a single sheet of tissue paper is utilized as the top tissue layer 66, the tissue paper should have an aperture formed in the tissue that coincides with the acquisition aperture 57 of the first layer 48. Alternatively, and most preferably, two separate pieces of tissue paper, first tissue layer 68 and second tissue layer 70, are positioned over the first layer 48 so that the tissue layers are laterally spaced from each other by at least a dimension equal in width to the width of the acquisition zone 56 or acquisition aperture 57 so as to form a tissue acquisition aperture 72.

As shown in FIG. 3, the topsheet 38 is preferably joined to the liquid handling layer 50 through the acquisition aperture 57 of the first layer 48 by attachment means 74 such as those well known in the art. For example, the topsheet 38 may be joined to the liquid handling layer 50 by a uniform continuous layer of adhesive, a patterned layer of adhesive, an array of separate lines or spots of adhesive, or by ultrasonically welding or bonding such as is known in the art. An adhesive which has been found to be satisfactory for use as the attachment means 74 is preferably a hot-melt adhesive such as manufactured by Eastman Chemical Products Company of Kingsport, Tennessee and marketed under the tradename of Eastobond A-3 or by Century Adhesives, Inc. of Columbus, Ohio and marketed under the tradename Century 5227. The attachment means 74 preferably comprises an open patterned network of filaments of adhesive as is shown in U.S. Pat. No. 4,573,986 entitled "Disposable Waste-Containment Garment", which issued to James A. Minetola and David R. Tucker on March 4, 1986, and which is incorporated herein by reference.

Absorbent core layers similar to the first layer 48 and the storage layer 52 can be formed by air-laying a dry mixture of hydrophilic fibers and particles of absorbent gelling material and densifying the resultant web. Such a procedure is described more fully in the hereinbefore referenced U.S. Pat. No. 4,610,678, entitled "High Density Absorbent Structures" which issued to Paul T. Weisman and Stephen A. Goldman on Sept. 9, 1986, which patent is incorporated herein by reference. The liquid handling layer 50 may be separately formed and inserted between the first layer 48 and the storage layer 52 or may be formed with the first layer 48 and the storage layer 52 in one process.

Without wishing to be bound by theory, it is believed that the absorbent core 42 described herein achieves a lower level of leakage of liquids in the following manner. Liquids, such as urine and other body exudates, that are deposited onto the topsheet 38 pass through the topsheet 38 to the acquisition zone 56. Since the acquisition zone 56 preferably comprises an acquisition aperture 57, and the topsheet 38 is joined to the liquid handling layer 50, there is lower resistance to the flow of liquid through the first layer 48 to the liquid handling layer 50. Because of the relatively high amount of void volume within the liquid handling layer 50, the liquid handling layer 50 acts as a reservoir to acquire the liquids within its structure. Due to the ability of the liquid handling layer 50 to transport liquid, the liquid is distributed to portions of the liquid handling layer 50 remote from the acquisition aperture 57. Due to the capillarity difference between the liquid handling layer 50 and the storage layer 52 (and preferably the holding zone 58), liquids are in essence "pumped" or drawn out of the liquid handling layer 50 and into the storage layer 52 wherein the absorbent gelling material and the hydrophilic fibers contain the liquid. The liquid handling layer 50 is thus drained of the initial gush of liquid, and because it is moisture insensitive, it has sufficient void volume to contain subsequent gushes of liquid, wherein the process described cycles again.

In use, the diaper 20 is applied to a wearer by positioning the back region 24 under the wearer's back, and drawing the remainder of the diaper 20 between the wearer's legs so that the front region 22 is positioned across the front of the wearer. The ends of the tape-tab fasteners 46 are then secured preferably to outwardly facing areas of the diaper 20. In use, disposable diapers or other absorbent articles having such absorbent cores 42 as described herein tend to more quickly acquire liquid into the absorbent core and remain dry or dryer due to the preferential capillarity of the absorbent core 42. Thus, such an absorbent core 42 helps to alleviate leakage around the edges of such absorbent articles.

Figure 5:
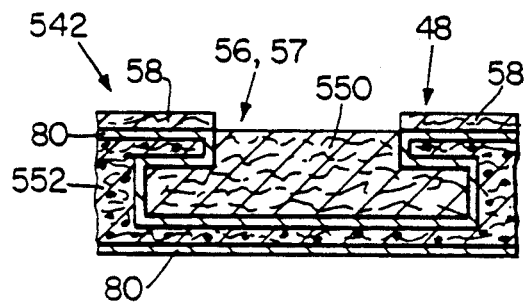
FIG. 5 is a fragmentary sectional view of an alternative embodiment of the absorbent core of the present invention.

FIG. 5 Shows an alternative embodiment of an absorbent core 542 of the present invention. As shown in FIG. 5, the storage layer 552 comprises a laminate of particles of absorbent gelling material overwrapped by a web 80 of fibrous material such as tissue paper. A preferred embodiment of this laminate is described in the hereinbeforementioned U.S. Pat. No. 4,578,608 issued to Kramer et al., which is incorporated herein by reference. This laminate is then C-folded around the liquid handling layer 550 into the configuration shown in FIG. 5 so as to encapsulate between the laminate the liquid handling layer 550. The liquid handling layer 550 has an inverted "T" cross-sectional area so that liquids acquired into the liquid handling layer 550 distribute rapidly to the edges of the storage layer 552 and are contained within the laminate and are not easily compressed out of such structure.

Figure 6:
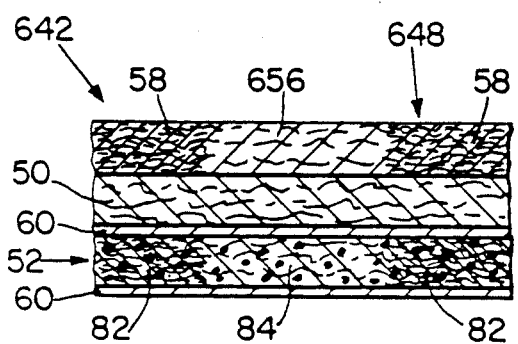
FIG. 6 is a fragmentary sectional view of a further alternative embodiment of the absorbent core of the present invention.

FIG. 6 shows a further alternative embodiment of an absorbent core 642 of the present invention. The first layer 648 is provided with an acquisition zone 656 that is not an aperture or hole but comprises the same material as the holding zone 58 comprising a mixture of hydrophilic fiber material and discrete particles of absorbent gelling material. This first layer 648 is similar in construction to the absorbent member described in The Procter & Gamble Company; European Patent Application EP-A-254,476; published Jan. 27, 1988. In addition, the storage layer 652 also comprises a storage layer holding zone 82 and a storage layer acquisition zone 84 so that liquids may be quickly acquired into the storage layer 52 through the storage layer acquisition zone 84 and rapidly wicked into the storage layer holding zone 82 where it is contained.

Figure 7:
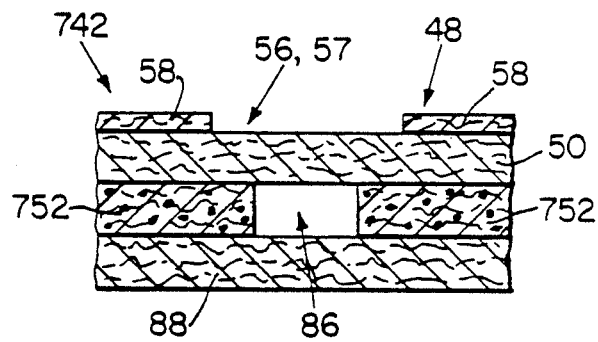
FIG. 7 is a fragmentary sectional view of a still further alternative embodiment of the absorbent core of the present invention.

FIG. 7 shows a still further alternative embodiment of an absorbent core 742 of the present invention. The storage layer 752 contains a storage layer acquisition zone preferably comprising a storage layer acquisition aperture 86. Additionally, a second liquid handling layer 88 is positioned subjacent the storage layer 752. Liquids deposited onto the absorbent core 742 are rapidly acquired by the acquisition zone 756 in the first layer 48, the first liquid handling layer 50, the storage layer acquisition aperture 86 in the storage layer 752, and the second liquid handling layer 88. Such a configuration effectively and efficiently uses both horizontal planes of the storage layer 752 to contain large gushes of liquids deposited onto the absorbent core 742. The liquid handling layer 50, the storage layer 752 and the second liquid handling layer 88 may alternatively have a laminate of absorbent gelling material such as previously described enwrapped or C-folded (such as the embodiment shown in FIG. 5) around them.

Figure 8:
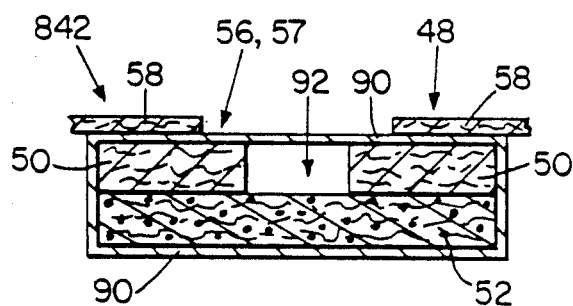
FIG. 8 is a fragmentary sectional view of an even further alternative embodiment of the absorbent core of the present invention.

FIG. 8 shows an even further alternative embodiment of an absorbent core 842 of the present invention. The storage layer 52 and the liquid handling layer 50 are wrapped in a web 90 of fibrous material such as tissue paper. In addition, the liquid handling layer 50 has a handling layer acquisition zone preferably comprising a handling layer acquisition aperture 92 to rapidly acquire liquids into the tissue enwrapped structure.

FIG. 9 is an even still further alternative embodiment of an absorbent core 942 of the present invention. The acquisition zone 956 in the first layer 48 preferably comprises a different material than the holding zone 58 (the remainder of the first layer 48). Preferably, the acquisition zone 956 comprises the same material as is used in the liquid handling layer 50. Most preferably, the acquisition zone 956 is formed from the same batt of fibers as the liquid handling layer 50 such that the acquisition zone 956 is unitary with the liquid handling layer 50, although embodiments where the acquisition zone is a separate layer from the liquid handling layer 50 are also contemplated. (It should also be noted that this drawing corresponds to the configuration generally assumed by the absorbent core 42 shown in FIGS. 1-4 after the absorbent core 42 has been processed and configured into a final diaper.)

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising:
a liquid pervious topsheet;
a liquid impervious backsheet joined with said topsheet; and
an absorbent core positioned between said backsheet and said topsheet, said absorbent core comprising:
a first layer comprising hydrophilic fibrous material, a holding zone, and an acquisition zone having a lower average density than said holding zone, said holding zone at least partially laterally surrounding the perimeter of said acquisition zone so as to be in liquid communication with at least a portion of the lateral area of said acquisition zone, said first layer being positioned between said topsheet and said backsheet;
a liquid handling layer positioned between said first layer and said backsheet and being subjacent at least said acquisition zone of said first layer, said liquid handling layer comprising a resilient material having gush handling capacity to receive quantities of body exudates, said liquid handling layer being moisture insensitive and having a percentage void volume greater than about 80%; and (c) a storage layer position between said backsheet and said liquid handling layer, said storage layer comprising a combination of fibrous material and discrete particles of absorbent gelling material.

2. The absorbent article of claim 1 wherein said liquid handling layer has a relatively lower capillarity than said storage layer.

3. The absorbent article of claim 2 wherein said liquid handling layer comprises a batt of synthetic fibers.

4. The absorbent article of claim 3 wherein said batt of synthetic fibers is bonded into an open structure with a caliper of greater than about 0.25 mm when measured under a load of about 0.1 psi.

5. The absorbent article of claim 4 wherein said batt of synthetic fibers has a void volume of at least about 5 cm³.

6. The absorbent article of claim 1 wherein said liquid handling layer comprises a synthetic foam.

7. The absorbent article of claim 1 wherein said acquisition zone comprises multiple acquisition apertures.

8. The absorbent article of claim 1 wherein said acquisition zone comprises an acquisition aperture.

9. The absorbent article of claim 8 wherein said acquisition aperture is rectangular shaped.

10. The absorbent article of claim 1 wherein said acquisition zone has a density and basis weight greater than zero and comprises the same material as said holding zone.

11. The absorbent article of claim 10 wherein said acquisition zone has a relatively lower average density and a lower average basis weight per unit area than said holding zone.

12. The absorbent article of claim 11 wherein said storage layer has a storage layer acquisition zone having a relatively lower average density than the remainder of said storage layer.

13. The absorbent article of claim 12 wherein said first layer additionally comprises from about 0% to about 8% by weight of said first layer of discrete particles of absorbent gelling material.

14. The absorbent article of claim 1 wherein said acquisition zone has a density and a basis weight greater than zero and comprises a different material than said holding zone.

15. The absorbent article of claim 14 wherein said acquisition zone comprises the same material as said liquid handling layer.

16. The absorbent article of claim 15 wherein said acquisition zone comprises a separate piece of material incorporated into said first layer.

17. The absorbent article of claim 15 wherein said acquisition zone is unitary with said liquid handling layer.

18. The absorbent article of claim 1 wherein said first layer additionally comprises from about 0% to about 8% by weight of said first layer of discrete particles of absorbent gelling material.

19. A disposable absorbent article comprising:
a liquid pervious topsheet;
a liquid impervious backsheet joined with said topsheet; and
an absorbent core positioned between said backsheet and said topsheet, said absorbent core comprising:
(a) a first layer comprising a web of hydrophilic fibrous material and having an acquisition aperture positioned in said first layer, said first layer being positioned between said topsheet and said backsheet;

(b) a liquid handling layer positioned between said first layer and said backsheet and being subjacent at least said acquisition aperture of said first layer, said liquid handling layer comprising a resilient batt of synthetic fibers having interstices to provide sufficient gush handling capacity to receive quantities of body exudates, said liquid handling layer being moisture insensitive and having a percentage void volume greater than about 80%; and (c) a storage layer positioned between said backsheet and said liquid handling layer, said storage layer comprising a combination of hydrophilic fibrous material and discrete particles of absorbent gelling material, wherein said liquid handling layer has a lower capillarity than said storage layer.

20. The absorbent article of claim 19 wherein said acquisition aperture has a top surface area less than about 35% of the total top surface area of said first layer.

21. The absorbent article of claim 20 wherein said acquisition aperture is positioned so that at least about 75% of the top surface area of said acquisition aperture is positioned in the front two-thirds section of said first layer.

22. The absorbent article of claim 21 wherein said topsheet is joined to said liquid handling layer through said acquisition aperture.

23. The absorbent article of claim 22 wherein said topsheet is spray-glued to said liquid handling layer.

24. The absorbent article of claim 22 additionally comprising a top tissue layer disposed between said topsheet and said first layer, said top tissue layer having a tissue acquisition aperture that coincides with said acquisition aperture.

25. The absorbent article of claim 24 wherein said top tissue layer comprises a first tissue layer and a second tissue layer laterally spaced from each other by at least about the width of said acquisition aperture so as to form said tissue acquisition aperture.

26. The absorbent article of claim 22 wherein said batt of synthetic fibers comprises polyester fibers.

27. The absorbent article of claim 26 wherein said first layer additionally comprises from about 0% to about 8% by weight of said first layer of discrete particles of absorbent gelling material.

28. The absorbent article of claim 27 wherein said storage layer has a top surface area which is from about 0.1 to about 1.0 times the top surface area of said first layer.

29. The absorbent article of claim 28 wherein said storage layer is enwrapped with a tissue layer.

30. The absorbent article of claim 29 wherein said acquisition aperture is rectangular shaped.

31. The absorbent article of claim 19 wherein said storage layer and said liquid handling layer are enwrapped with a web of material.

32. The absorbent article of claim 31 wherein said liquid handling layer has a handling layer acquisition aperture.

33. The absorbent article of claim 19 wherein said storage layer has a storage layer acquisition zone of a lower average density than the remainder of said storage layer.

34. The absorbent article of claim 33 wherein said storage layer acquisition zone comprises a storage layer acquisition aperture.

35. The absorbent article of claim 34 additionally comprising a second liquid handling layer positioned subjacent said storage layer.

36. The absorbent article of claim 19 wherein said storage layer comprises a laminate of particles of absorbent gelling material overwrapped by a web of fibrous material.

37. The absorbent article of claim 36 wherein said laminate is C-folded around said liquid handling layer.

38. The absorbent article of claim 37 wherein said liquid handling layer has an inverted T cross-sectional area.

39. A disposable diaper comprising:
a liquid pervious topsheet;
a liquid impervious backsheet joined with said topsheet; and
an absorbent core positioned between said backsheet and said topsheet, said absorbent core comprising:
(a) a first layer comprising a web of hydrophilic fibrous material and from 0% to about 8% by weight of said first layer of discrete particles of absorbent gelling material, said first layer having an acquisition aperture completely positioned in the front two-thirds section of said first layer, said acquisition aperture having a top surface area less than about 20% of the total top surface area of said first layer, said first layer being positioned between said topsheet and said backsheet;
(b) a liquid handling layer positioned between said first layer and said backsheet and being subjacent at least said acquisition aperture of said first layer, said liquid handling layer comprising a resilient batt of synthetic fibers having interstices to provide sufficient gush handling capacity to receive quantities of body exudates, said liquid handling layer being moisture insensitive, having a percentage void volume greater than about 90%, and having a void volume of at least about k10 cm$^3$; and
(c) a storage layer positioned between said backsheet and said liquid handling layer, said storage layer comprising an admixture of hydrophilic fibrous material and discrete particles of absorbent gelling material,
wherein said liquid handling layer has a relatively lower capillarity than said storage layer and said web of said first layer.

40. The disposable diaper of claim 39 wherein said topsheet is joined to said liquid handling layer through said acquisition aperture.

41. The disposable diaper of claim 40 wherein said storage layer has a top surface area which is from about 0.1 to about 1.0 times that of said first layer, and said liquid handling layer has a top surface area which is from about 0.8 to about 1.0 times that of said storage layer.

42. The disposable diaper of claim 41 wherein said batt of synthetic fibers of said liquid handling layer comprises polyester fibers bonded into an open structure with a caliper of greater than about 0.38 mm.

* * * * *